(12) United States Patent
Presser et al.

(10) Patent No.: US 8,455,843 B1
(45) Date of Patent: Jun. 4, 2013

(54) ULTRAVIOLET IONIZING CHAMBER FOR AIR PURIFIERS

(71) Applicant: Presser Direct LLC, Los Angeles, CA (US)

(72) Inventors: Mark Presser, Los Angeles, CA (US); Ira Smolens, Boca Raton, FL (US)

(73) Assignee: Presser Direct LLC, Los Angeles, CA (US)

( * ) Notice: Subject to any disclaimer, the term of this patent is extended or adjusted under 35 U.S.C. 154(b) by 0 days.

(21) Appl. No.: 13/646,387

(22) Filed: Oct. 5, 2012

(51) Int. Cl.
*G21K 5/00* (2006.01)
(52) U.S. Cl.
CPC .................................. *G21K 5/00* (2013.01)
USPC ..................................... 250/455.11; 422/121
(58) Field of Classification Search
USPC ................. 250/455.11, 454.11; 422/120, 121
See application file for complete search history.

(56) References Cited

U.S. PATENT DOCUMENTS

2010/0260644 A1* 10/2010 Day et al. ...................... 422/121
2011/0006216 A1* 1/2011 Searle ...................... 250/455.11

* cited by examiner

*Primary Examiner* — Kiet T Nguyen
(74) *Attorney, Agent, or Firm* — Daniel R. Kimbell

(57) ABSTRACT

An ultraviolet ionizing unit for an air purifying that treats all air passing therethrough. The unit has a housing with an air ingress opening at first end, an air egress opening at a second end, an open end, at least two spaced apart internal retainers formed inside the housing, and a cavity formed in a space between the two spaced apart internal retainers. Two sections of ion generating material are retained in a spaced apart manner by the two spaced apart internal retainers. Spacers are used to hold a U-shaped UV lamp in the cavity, provide cushioning of the UV lamp therein, and providing additional sealing so that all air passing through the ionizing unit will be treated. A housing end cap covers the open end of the housing and retains the UV lamps therein so that the ion generating materials is fully exposed by UV light.

12 Claims, 7 Drawing Sheets

ULTRAVIOLET IONIZING CHAMBER FOR AIR PURIFIERS

BACKGROUND OF THE INVENTION

The present invention relates generally to air purifiers for cleaning air, and more particularly to an ultraviolet ionizing chamber for portable air purifiers, which ultraviolet ionizing chamber helps to eliminate contaminants from the air being treated, including biospecies, dust particles, odors, and volatile organic chemicals.

The presence of airborne biospecies (e.g., dust mites, bacteria, viruses, and fungi), dust particles, pollen, odors, and volatile organic chemicals can exacerbate allergies in people sensitive to these agents. Moreover, contaminated surfaces in hospitals and health care facilities—such as counter tops, beddings, bed pans, and medical devices—have been identified as the cause of spread of infections and disease. The Centers for Disease Control and Prevention (CDC) estimates 1.7 million hospital associated infections in the US every year, 99,000 out of those may result in death (Klevens and others 2007). Indoor air is also recognized as major vector of nosocomial infections, the infections that may be acquired in a hospital or health care facility. Methicillin resistant Staphylococcus aureus (MRSA), a type of S. aureus that is resistant to beta-lactams antibiotics, is a bacterium that causes infections of skin, and is identified as the common cause of health care associated infections (HAIs). CDC surveillance data reveals 58.4% MRSA infections were community-onset, 26.6% were hospital-onset, 13.7% were community-associated, while 1.3% were unclassified (Klevens and others 2007).

There is an ever growing need for development and evaluation of technologies aimed at reducing environmental contamination and improving the quality of indoor air that we breathe. Accordingly, a variety of devices and methods have used to purify air. These include air filtration, the use of charged plates, and UV light, among others. However, the efficacy of some of these devices can be limited due to their inability to remove nearly all of the airborne agents.

There accordingly remains a need for a highly effective device which will remove a very high percentage, e.g., 95%, and preferably 98% or more of these agents on a single pass of air through an air purification unit.

SUMMARY OF THE INVENTION

The invention is an ultraviolet ionizing chamber for portable air purifiers, which ultraviolet ionizing chamber helps to eliminate contaminants from the air being treated including airborne biospecies (e.g., dust mites, bacteria, viruses, and fungi), dust particles, pollen, odors, and volatile organic chemicals.

In one embodiment the invention provides an ultraviolet ionizing unit for an air purifying, the ultraviolet ionizing unit comprising: a housing having a top wall, an end wall, and a bottom wall, with an open front, an air ingress opening, an air egress opening, at least two spaced apart internal retainers formed inside the housing, and a cavity formed in a space between the two spaced apart internal retainers; two sections of ion generating material, one each retained by the two spaced apart internal retainers; a housing end cap that covers the open front of the housing and retains the two sections of ion generating material therein; a U-shaped UV light source with two generally parallel portions, a U-shaped portion joining the two generally parallel portions, and two ends with electrical leads, the U-shaped UV light source being positioned in the cavity; and spacers that hold the U-shaped UV light source in the cavity and provide cushioning of the UV light source therein.

In another embodiment the invention provides a: An ultraviolet ionizing unit for an air purifying, the ionizing unit comprising: a housing with an air ingress opening at first end, an air egress opening at a second end that is opposite the first end, and an open end, at least two spaced apart internal retainers formed inside the housing, and a cavity formed in a space between the two spaced apart internal retainers; two sections of ion generating material, one each retained in a spaced apart manner by each of the two spaced apart internal retainers; a housing end cap that covers the open end of the housing; a U-shaped UV light source with two generally parallel portions, a U-shaped portion joining the two generally parallel portions, and two ends with electrical leads, the U-shaped UV light source being positioned in the cavity; and spacers that hold the U-shaped UV light source in the cavity and provide cushioning of the UV light source therein.

DETAILED DESCRIPTION

Figure 1:
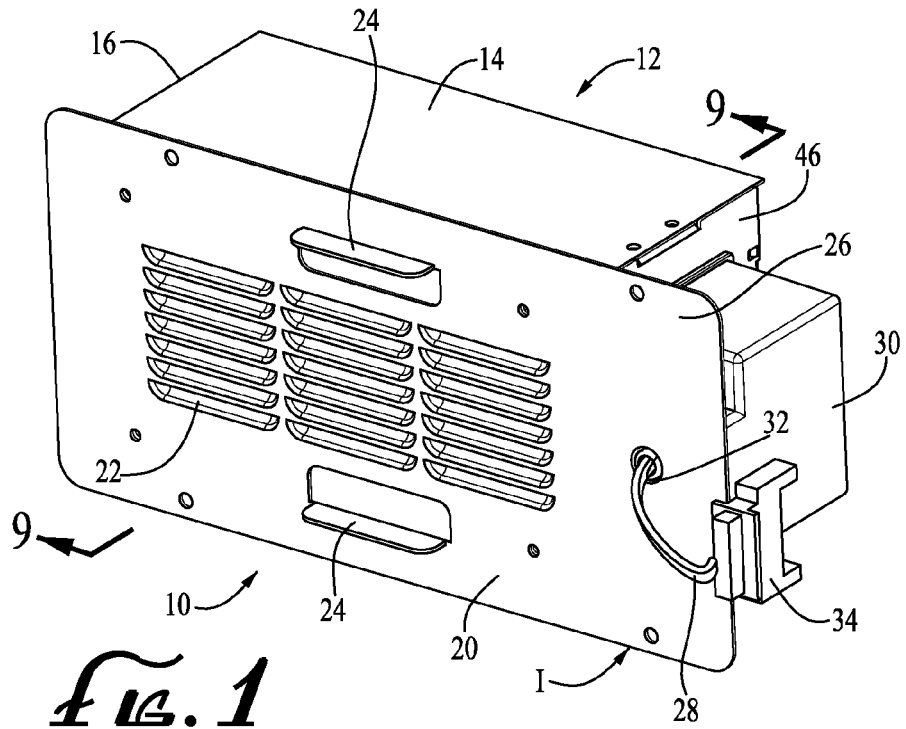
FIG. 1 is a front perspective view of an exemplary ultraviolet ionizing chamber of the invention.
Figure 2:
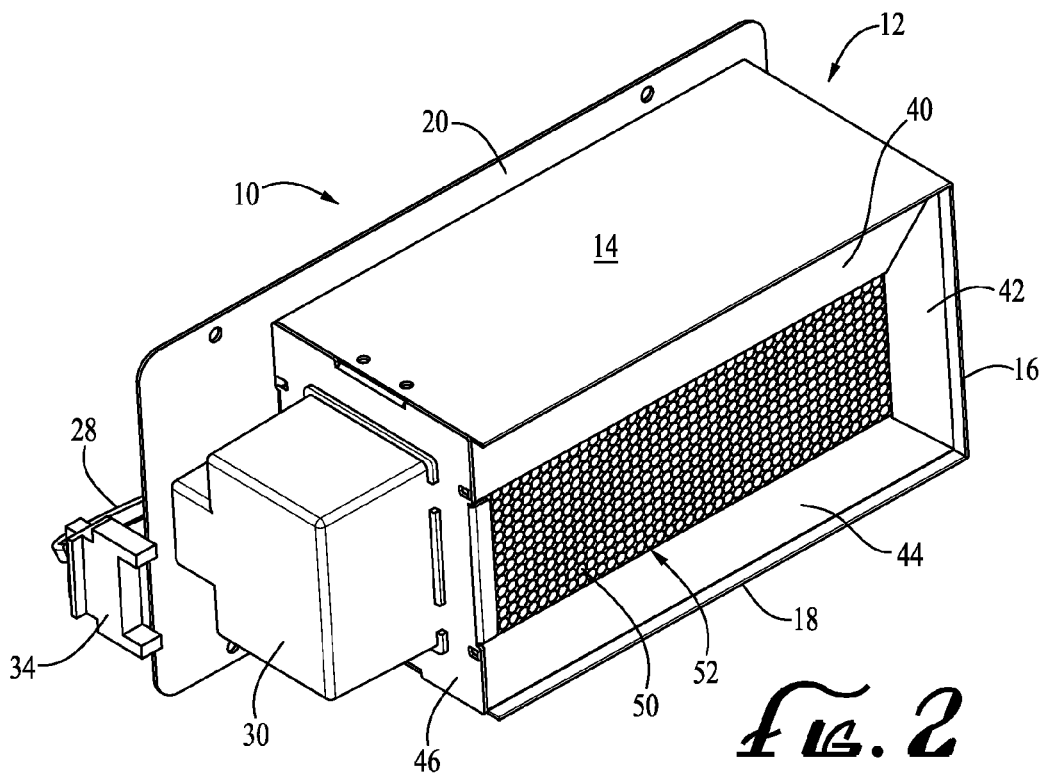
FIG. 2 is a rear perspective view thereof.

Turning first to FIGS. 1 and 2, there are shown, respectively, front and rear perspective views of an exemplary ultraviolet ionizing chamber 10 of the invention. The ultraviolet ionizing chamber 10 has a housing 12 with a top wall 14, an end wall 16, a bottom wall 18, and a front grill/mounting plate 20. The front grill/mounting plate 20 has a grid opening 22 providing openings for air to enter the ionizing chamber 10. The front grill/mounting plate 20 is at an air ingress side "I" of thereof. For ease of handling the ionizing chamber 10, two finger grips 24 can be provided. The finger grips 24 can comprise two spaced apart rectangular ears that are bent outwardly from the front grill/mounting plate 20. The front grill/mounting plate 20 has a rim 26 that provides a surface for attaching to an air purification system (not shown) and provide airtight sealing therewith, to ensure that all the air entering the air purification system must pass through the ultraviolet ionizing chamber 10 so that all air, rather than just a portion of the air, is treated. A power cord 28 from a light source electronics housing 30 passes through a hole 32 in the front grill/mounting plate 20. A power connector 34 is on the end of the power cord 28. The housing 12 has rear rim section 40, 42, and 44 that extend from at or near back edges of the top wall 14, the end wall 16, and the bottom wall 18, respectively. A housing end cap 46 carrying the light source electronics housing 30 is detachably connected to the housing 12. A section of honeycomb material 50 is positioned at an air egress side 'E' of the housing and can be seen through an egress window 52 defined by the housing end cap 46 and rear rim section 40, 42, and 44.

Figure 3:
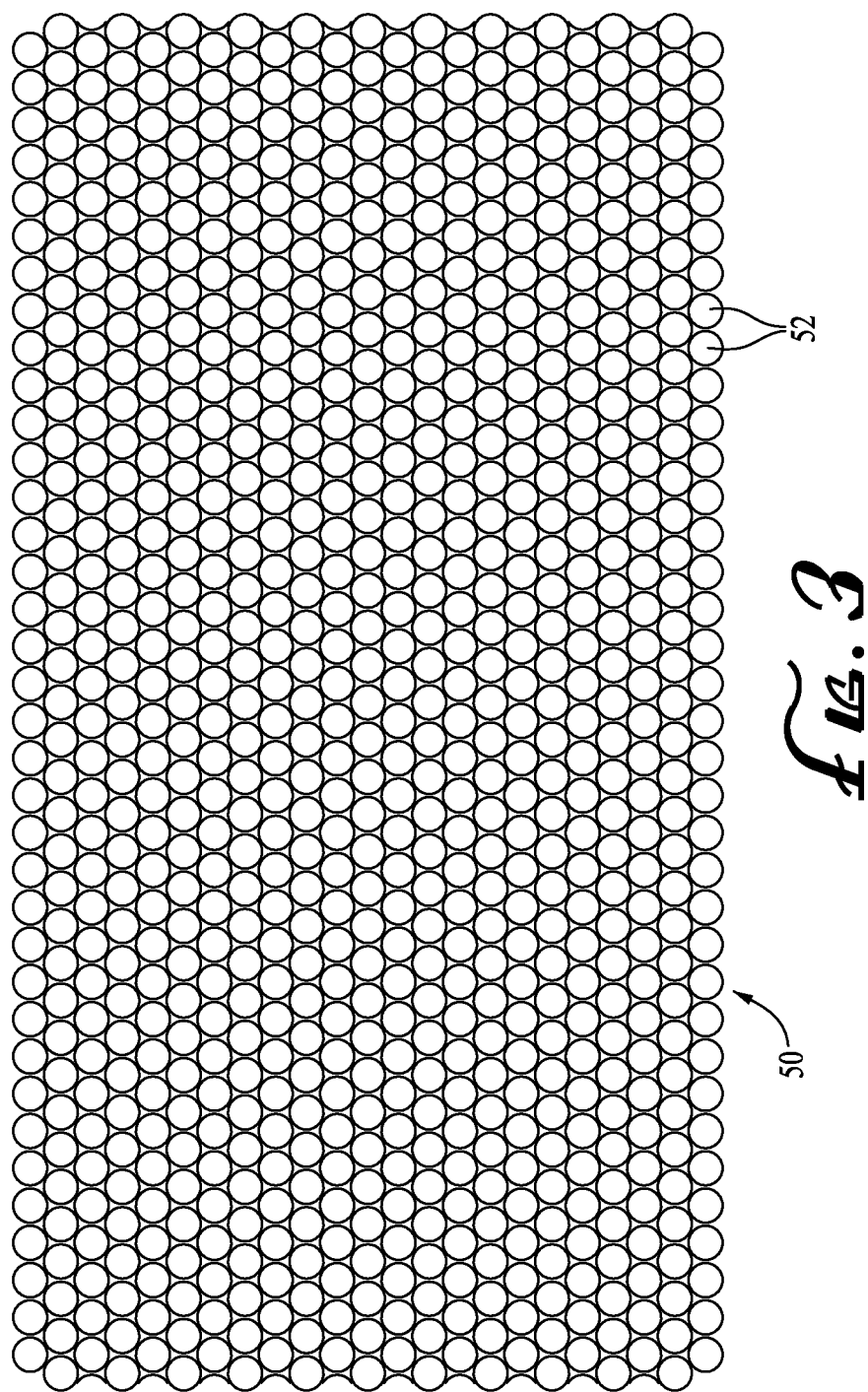
FIG. 3 is a top plan view of an exemplary section honeycomb material treated with titanium dioxide, which used in the ionizing chamber.

FIG. 3 is a top plan view of an exemplary section of honeycomb material 50 treated with titanium dioxide, which honeycomb material is used in the ionizing chamber. The honeycomb material can be a plastic material, with a grid of tubular sections 52 that are interconnected. In one embodiment, tubes have a diameter of about 4 mm is used. The honeycomb material can be of a desired thickness, and a thickness of about 14 mm functions well. The tubes 52 making up the honeycomb material 50 have passages therethrough. When installed in the housing 12 of the ionizing chamber, the axes of the tubes 52 will be aligned with the air flow and will generate positive and negative ions. This material will sometimes be referred to herein as ion generating material.

Such a material provides minimal interruption of airflow therethrough. As will be discussed further below, when the titanium dioxide is activated by the high intensity UV light emanating from the UV light source, e.g., a UV lamp (shown in FIGS. 4, 6, and 8), will generate positive and negative ions, which ions will almost instantaneously cause contaminants in the air being treated to clump together, and fall from the air. Furthermore, illumination of the titanium dioxide on the honeycomb material will likewise generate hydrogen peroxide, which is a powerful oxidizing agent to deactivate biospecies (e.g., dust mites, bacteria, viruses, and fungi), dust particles, pollen, odors, and volatile organic chemicals. The ratio of the length of the tube to the diameter of the tube should not be too large so that the entire surface of the titanium dioxide coated honeycomb material can be bathed in UV light. Although material having a honeycomb structure is one preferred type of material, other materials can be used if desired, such as webbed material having a number of strands coated with titanium dioxide (or other materials) that provide the ionizing effect when irradiated with UV light. An important consideration in selection of the material being that air flow not be overly impeded and that the titanium dioxide coating be adapted to be bathed with UV light.

Figure 4:
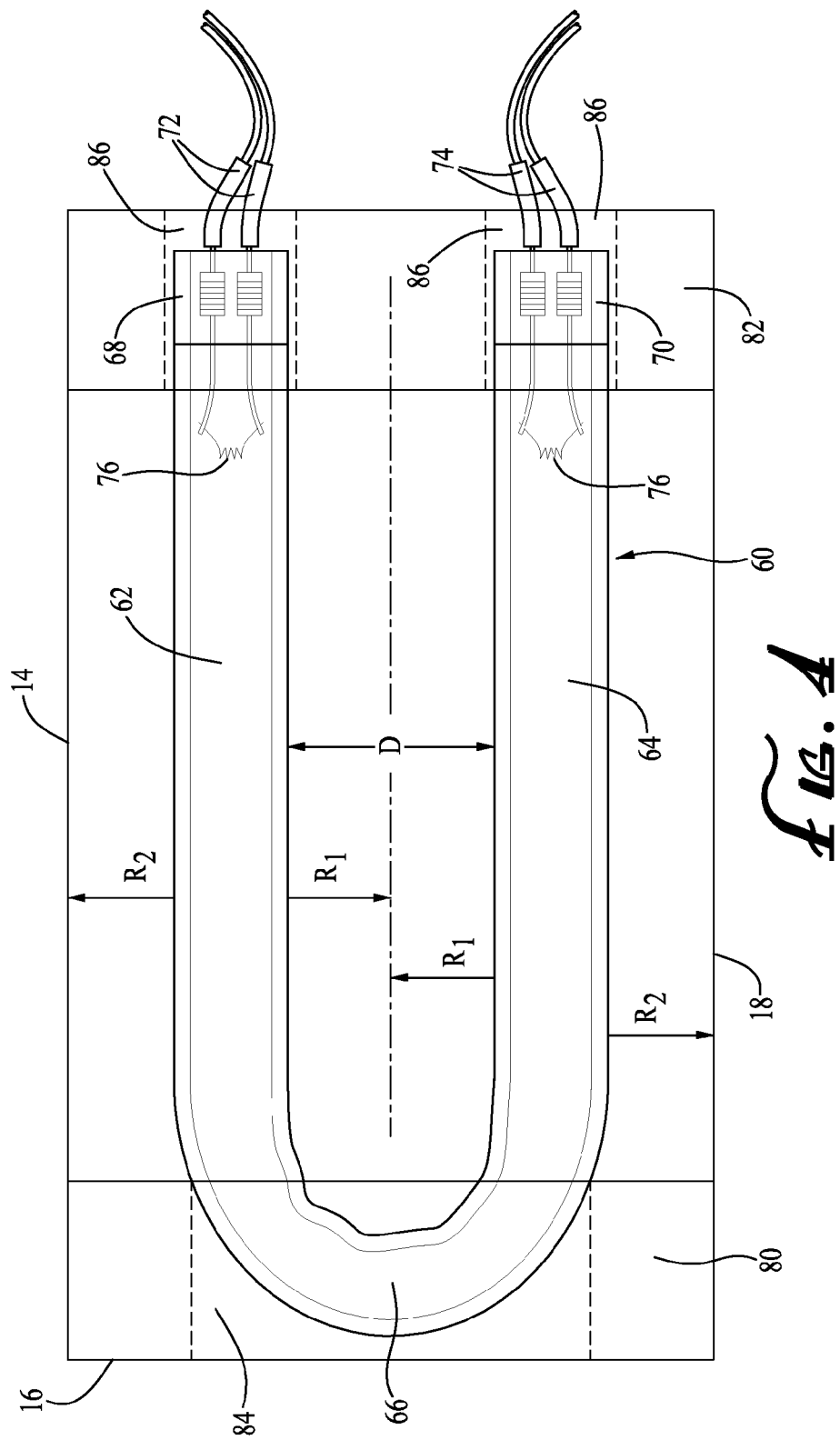
FIG. 4 is a top plan view of an exemplary UV light source of the invention.

FIG. 4 is a top plan view of an exemplary UV light source 60 of the invention. The UV light source 60 can preferably comprise a UV lamp with a U-shaped configuration, with two parallel elongate sections 62 and 64, joined with a U-shaped end 66. At the ends 68 and 70 of the elongate sections 62 and 64, respectively, are pairs of electrical leads 72 and 74 for energizing filaments 76 in the tubing. An outline of the top wall 14, end wall 16, and bottom wall 18 of the housing 12 is shown. An outline of front spacer 80 and rear spacer 82 are shown. The spacers 80 and 82 can be formed of foam rubber or other material and help prevent shocks to the unit from damaging the UV light source 60. A channel 84 can be cut in the front spacer 80 to hold the U-shaped 66 front end of the UV light source 60 and two slots 86 cut in the rear spacer 82 to suspend the ends of the elongate sections 62 and 64. The spacers 80 and 82 also serve another purpose in that they impede airflow therethrough, forcing air that passes through the ultraviolet ionizing chamber 10 to be exposed to UV light from the UV light source 60. As can be see, the distance $R_1$ from the two parallel elongate sections 62 and 64 to a centerline "CL" between the two sections, and the distance $R_2$ from the two parallel elongate sections 62 and 64 to the walls 14 and 18 are likewise minimized.

Figure 5:
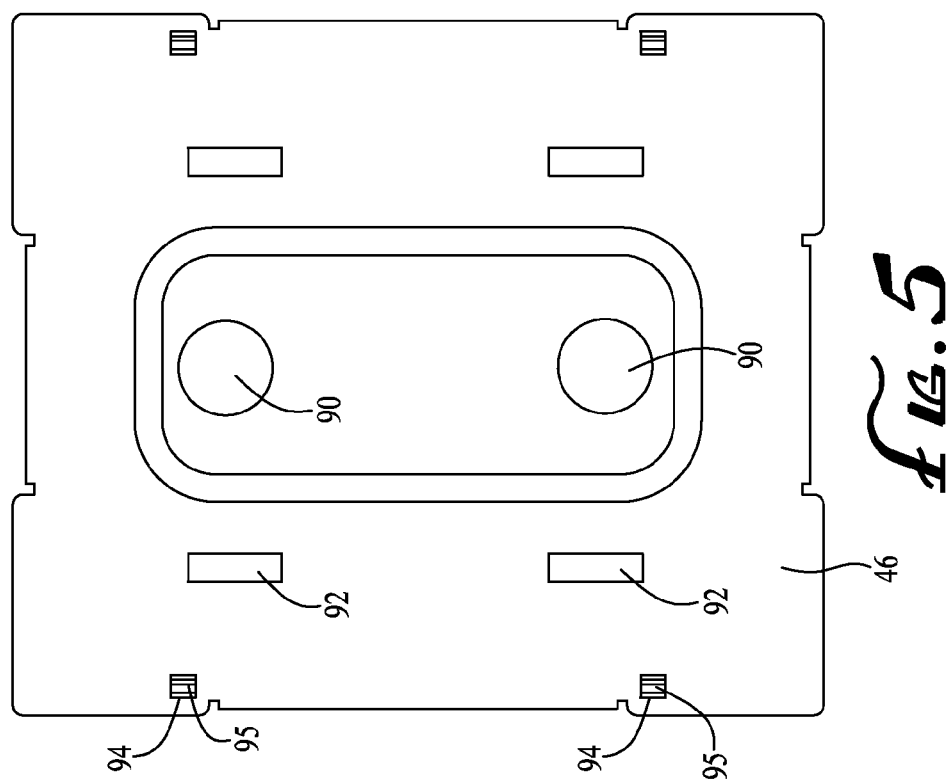
FIG. 5 is a top plan view of an exemplary housing end cap.

FIG. 5 is a top plan view of an exemplary housing end cap 46. It includes a plate 46 and two apertures 90 for passage of the pairs of electrical leads 72 and 74 (not shown.) The plate 46 also can have apertures 92, the purposes of which is to retain complementary tab (not shown) on the light source electronics housing 30 to hold it in place to the housing end cap 46. Rectangular ears 94 formed by cutouts in the plate 46 are provided to engage and interlock with slots formed on the housing, as described below.

Figure 6:
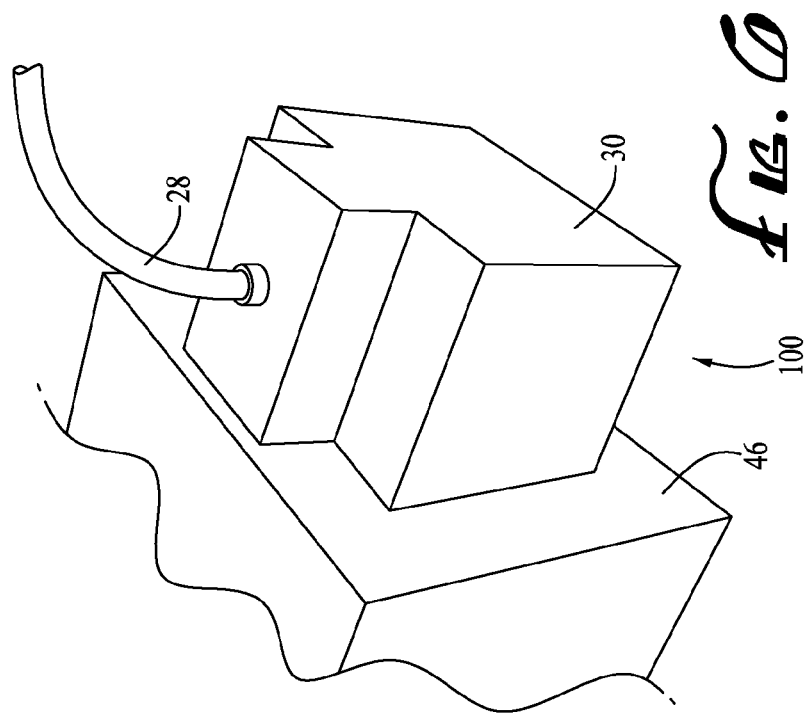
FIG. 6 is a perspective view of an exemplary electronics housing/housing end cap unit.

FIG. 6 is a perspective view of an exemplary electronics housing/housing end cap unit 100. The light source electronics housing 30 is shown attached to the exemplary housing end cap 46 with its power cord 28 extending therefrom. The UV light source 60 is connected to the electronics housing/housing end cap unit 100 and during assembly of the ionizing chamber 10, the UV light source 60 and its connected electronics housing/housing end cap unit 100 will be engaged with the housing, as shown in FIG. 8.

Figure 7:
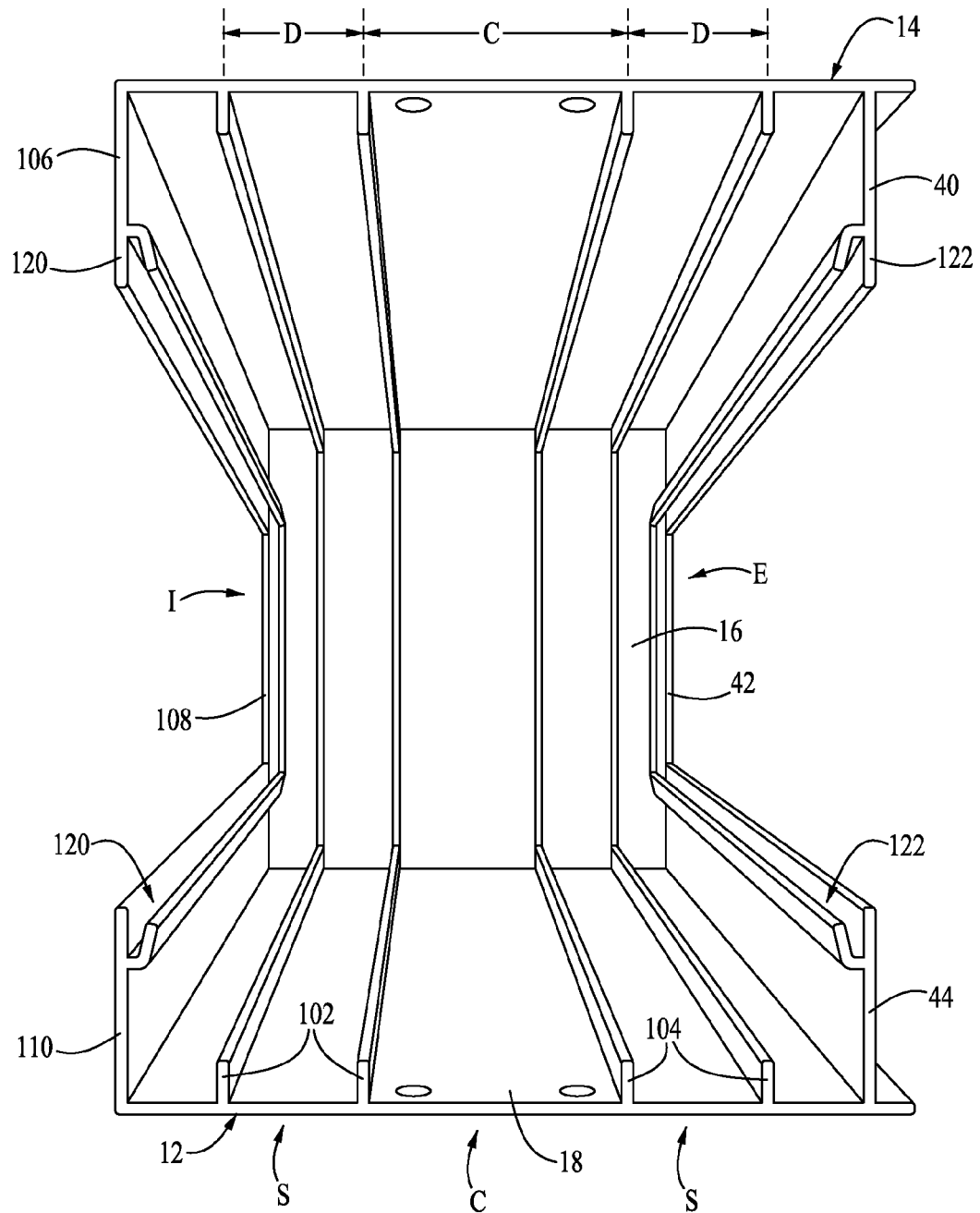
FIG. 7 is front perspective view of an exemplary housing for the ionizing chamber, with other components removed.

FIG. 7 is front perspective view of an exemplary housing 12 for the ionizing chamber 10, with other components removed. The extending inwardly from the top wall 14, end wall 16, and bottom wall 18 are pairs of spaced apart retention rails 102 and 104. The each of the retention rails in the pairs of retention rails 102 and 104 are spaced apart by a distance D that is approximately the same as the thickness of the sections of honeycomb material so that when the sections of honeycomb material are engaged in the housing 12, any air passing through the ultraviolet ionizing chamber 10 will be forced to travel through the sections of honeycomb material. The pairs of spaced apart retention rails 102 and 104 establish retainers, or slots "S", for receipt of the sections of honeycomb material. The two pairs of retention rails 102 and 104 in turn spaced apart by distance C, which defines a cavity into which the UV light source will be located. While such retention rails 102 and 104 are shown on the top wall 14, end wall 16, and bottom wall 18, due to the presence of the front spacer 80 (see FIGS. 4 and 8) which will tend to prevent leakage of air at the end wall 16, the use of retention rails on the end wall 16 is optional. The ingress end "I" and egress end "E" are shown. Rim portions 106, 108, and 110 extend from the top wall 14, end wall 16, and bottom wall 18, respectively, and are formed at an ingress end I of the housing 12. This provides a surface for attachment of the front grill/mounting plate 20. Located around terminal ends of the rim portions 106, 108, and 110 is a front groove 120. Located around terminal ends of the rear rim sections 40, 42, and 44 is a rear grove 122. The front and rear grooves 120 and 122 provide openings into which rectangular ears 94 formed by cutouts in the housing end cap 46 (see FIG. 5) engage. The housing 12 can conveniently be formed of extruded material (e.g., aluminum, plastic, etc.) having the described profile. This arrangement of the wall sections 14, 16, and 18 provides a housing into which the sections of honeycomb material can easily be slid into during assembly, and with the UV bulb and its connected electronics housing/housing end cap unit 100 engaged therewith.

Figure 8:
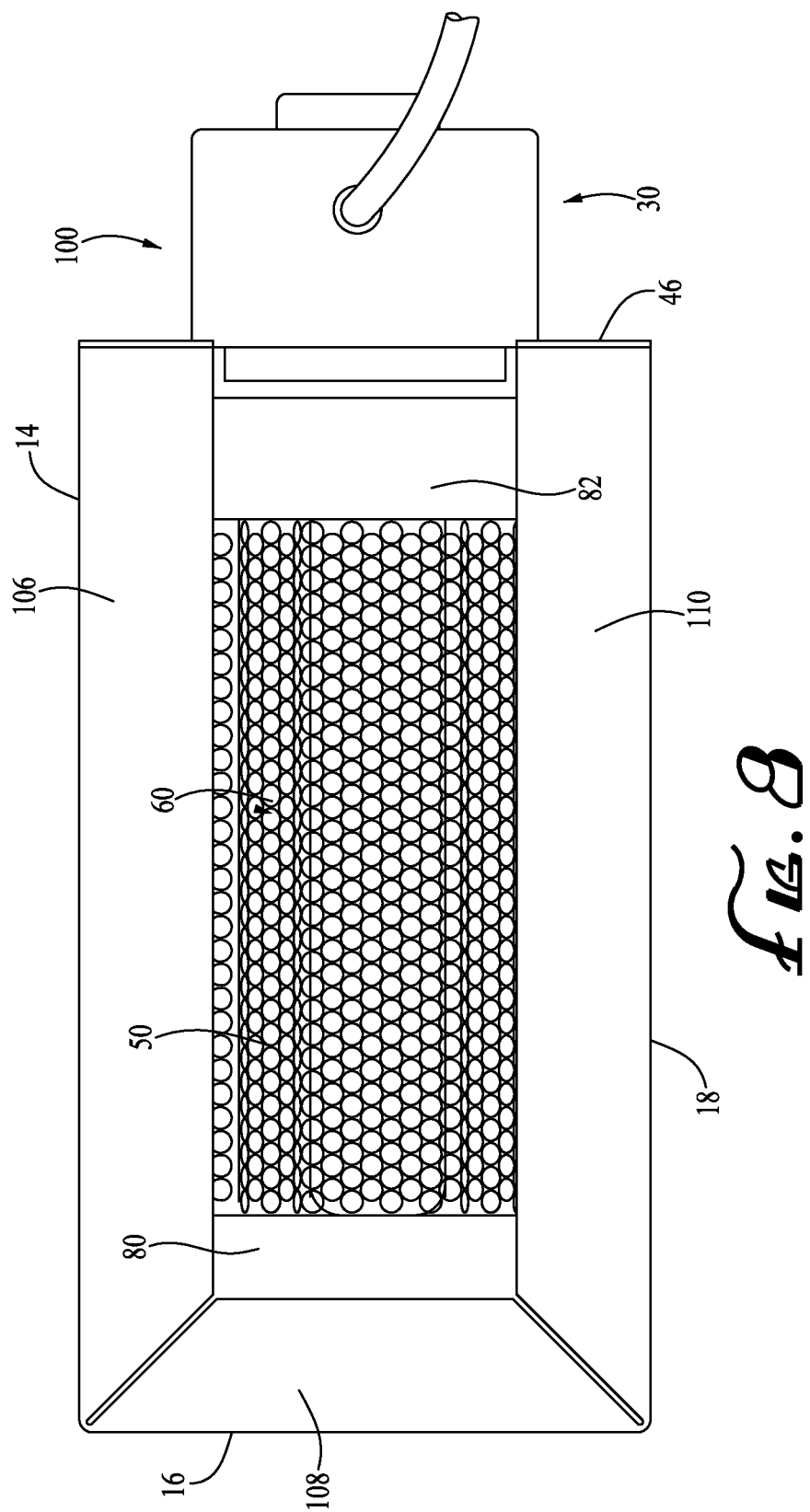
FIG. 8 is a front perspective view of an exemplary housing for the ionizing chamber, with its light source electronics housing/housing end cap and a downstream section of honeycomb material in place, but with the upstream section of honeycomb material and the option front grill removed.

FIG. 8 is a front perspective view showing an ingress opening in the exemplary housing for the ionizing chamber 12, with its light source holder/housing end cap 100 (having end cap 46 and light source electronic housing 30) and a downstream section of honeycomb material 50 in place, but with the upstream section of honeycomb material and the option front grill removed. The rim portion 106, 108, and 110 extending from wall 14, 16, 18, respectively, are shown. Also shown are UV light source 60, and spacers 80 and 82.

Figure 9:
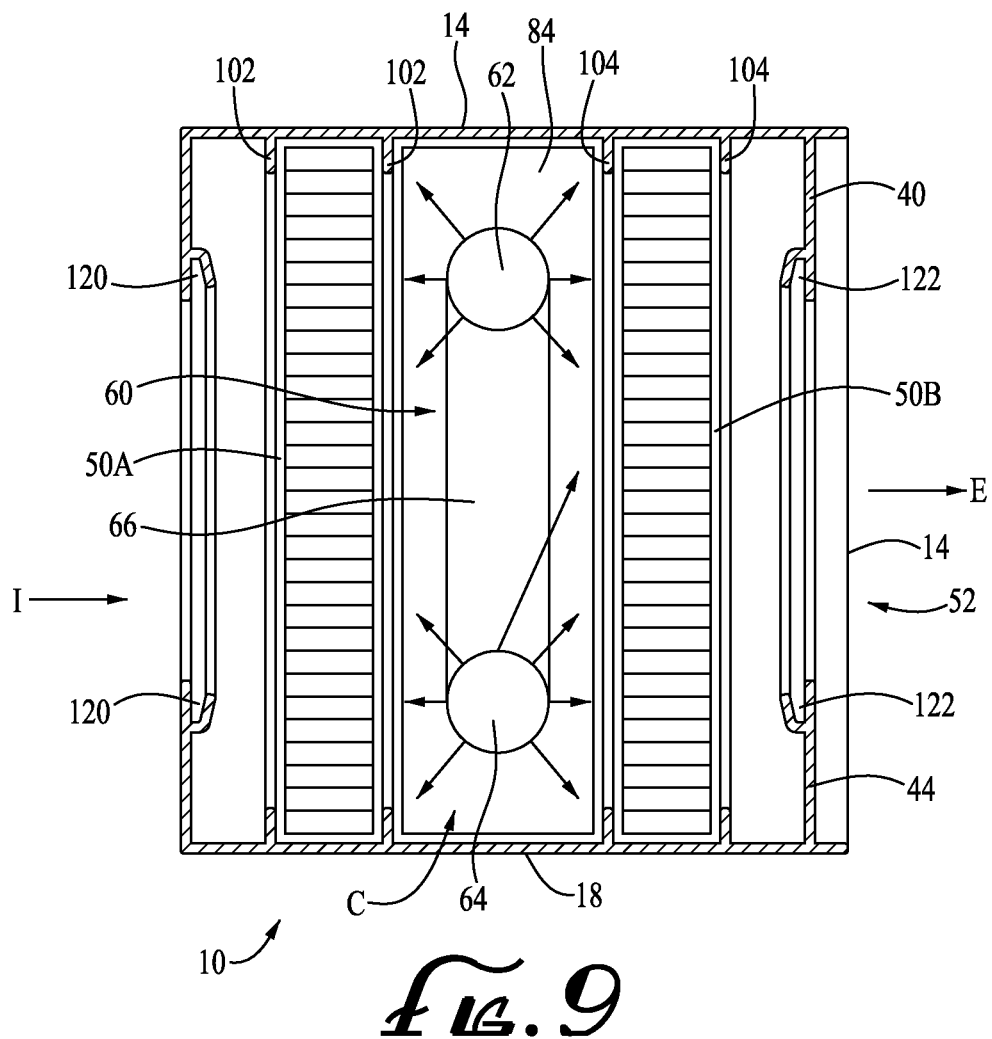
FIG. 9 is a cross-sectional view through view lines 9-9 of FIG. 1.

FIG. 9 is a cross-sectional view of the assembled ultraviolet ionizing chamber 10 (less the front grill/mounting plate) through view lines 9-9 of FIG. 1. As can be seen, the sections of honeycomb material 50A and 50B are snuggly positioned in the housing 12 within the pairs of retention rails 102 and 104, respectively. The U-shaped UV light source 60 with its two parallel sections 62 and 64 will provide for generally uniform bathing of the two section of honeycomb material 50 with UV light, and will force the air that passes through ingress end "I", through the first section of honeycomb material 50A, pass through the cavity C with the UV bulb 60, then through the second section of honeycomb material 50B and out the egress end E through the egress window 52. The unique construction of the housing 12 which tightly carries the two sections of honeycomb material and the positions the UV bulb 60 provides for full treatment of air passing through the ultraviolet ionizing chamber 10 and reduces airborne contaminants by 98% or more in a single pass. In operation, air will pass through the ultraviolet ionizing chamber 10 many times a day and substantially all airborne contaminants will be eliminated. Moreover, the electronics housing/housing end cap unit 100 which carries the U-shaped bulb 60 provides ease of assembly.

The preferred embodiments of this invention have been disclosed, however, so that one of ordinary skill in the art would recognize that certain modifications would come within the scope of this invention. It is, therefore, to be understood that within the scope of the appended claims, the invention may be practiced otherwise than as specifically described.

What is claimed is:

1. An ultraviolet ionizing unit for an air purifying, the ionizing unit comprising:
    a housing having a top wall, an end wall, and a bottom wall, with an open front, an air ingress opening, an air egress opening, at least two spaced apart internal retainers formed inside the housing, and a cavity formed in a space between the two spaced apart internal retainers;
    two sections of ion generating material, one each retained by the two spaced apart internal retainers;
    a housing end cap that covers the open front of the housing and retains the two sections of ion generating material therein;
    a U-shaped UV light source with two generally parallel portions, a U-shaped portion joining the two generally parallel portions, and two ends with electrical leads, the U-shaped UV light source being positioned in the cavity; and
    spacers that hold the U-shaped UV light source in the cavity and provide cushioning of the UV light source therein.

2. The ultraviolet ionizing unit of claim 1, wherein the two spaced apart internal retainers formed inside the housing each comprising a pair of parallel walls that extend inwardly into the housing and define rails, the rails being present on at least portions of the top wall and the bottom wall.

3. The ultraviolet ionizing unit of claim 2, wherein the two sections of ion generating material comprising honeycomb material with titanium dioxide on surfaces thereof, with the sections of honeycomb material having a thickness adapted to snugly fit with the pairs of rails.

4. The ultraviolet ionizing unit of claim 1, further comprising a light source electronics housing that is fixed to the housing end cap.

5. The ultraviolet ionizing unit of claim 1, wherein the spacers comprise two sections of cushioning material, with a first section being adapted to hold the front U-shaped portion of the UV light source, and with a second section being adapted to hold two terminal ends of the U-shaped UV light source and have electrical leads pass therethrough.

6. The ultraviolet ionizing unit of claim 1, wherein the spacers comprise foam material which are located in the cavity between the two spaced apart internal retainers.

7. The ultraviolet ionizing unit of claim 1, further comprising a front grill/mounting plate that is positioned at the air ingress end of the housing, and which front grill/mounting plate is adapted for mounting of the ionizing unit.

8. An ultraviolet ionizing unit for an air purifying, the ionizing unit comprising:
    a housing with an air ingress opening at first end, an air egress opening at a second end that is opposite the first end, and an open end, at least two spaced apart internal retainers formed inside the housing, and a cavity formed in a space between the two spaced apart internal retainers;
    two sections of ion generating material, one each retained in a spaced apart manner by each of the two spaced apart internal retainers;
    a housing end cap that covers the open end of the housing;
    a U-shaped UV light source with two generally parallel portions, a U-shaped portion joining the two generally parallel portions, and two ends with electrical leads, the U-shaped UV light source being positioned in the cavity; and
    spacers that hold the U-shaped UV light source in the cavity and provide cushioning of the UV light source therein.

9. The ultraviolet ionizing unit of claim 8, wherein each of the two spaced apart internal retainers formed inside the housing comprises a pair of spaced apart parallel walls that extend inwardly into the housing and define rails, the rails being present on at least portions of the top wall and the bottom wall, with the two walls being spaced apart by a distance that is approximately the same as a thickness of the sections of ion generating material, such when the sections of ion generating material are engaged with the rails, air will be forced to pass through the two sections of ion generating material.

10. The ultraviolet ionizing unit of claim 8, wherein the two sections of ion generating material comprising honeycomb material with titanium dioxide on surfaces thereof.

11. The ultraviolet ionizing unit of claim 8, wherein the spacers comprise foam cushioning material, with a first spacer being adapted to hold the front U-shaped portion of the UV light source, and with a second spacer being adapted to hold two terminal ends of the U-shaped UV light source and have electrical leads pass therethrough, and wherein the spacers further providing sealing to help prevent air passing through the ionizing unit from bypassing the ion generating material and exposure to UV light.

12. The ultraviolet ionizing unit of claim 8, further comprising a front grill/mounting plate that is positioned at the air ingress end of the housing, and which front grill/mounting plate is adapted for mounting of the ionizing unit.

* * * * *